United States Patent [19]
Wada et al.

[11] 3,954,855
[45] May 4, 1976

[54] PROCESS FOR PREPARING ACRYLIC ACID

[75] Inventors: Masahiro Wada, Nishinomiya; Isao Yanagisawa, Ikeda; Michikazu Ninomiya, Kobe; Takashi Ohara, Nishinomiya, all of Japan

[73] Assignee: Nippon Shokubai Kagaku Kogyo Co. Ltd., Osaka, Japan

[22] Filed: Mar. 18, 1974

[21] Appl. No.: 452,348

[30] Foreign Application Priority Data

Mar. 22, 1973 Japan.............................. 48-31830

[52] U.S. Cl............................ 260/530 N; 252/456; 252/467
[51] Int. Cl.²............... C07C 51/26; C07C 57/04
[58] Field of Search................... 260/530 N, 533 N

[56] References Cited
UNITED STATES PATENTS

| | | |
|---|---|---|
| 3,567,773 | 3/1971 | Yamaguchi et al............. 260/530 N |
| 3,775,474 | 11/1973 | Ohara et al..................... 260/530 N |
| 3,799,978 | 3/1974 | Ohara et al..................... 260/533 N |

FOREIGN PATENTS OR APPLICATIONS

| | | |
|---|---|---|
| 2,152,037 | 5/1972 | Germany......................... 260/530 N |

*Primary Examiner*—Richard L. Raymond
*Attorney, Agent, or Firm*—Sherman & Shalloway

[57] ABSTRACT

A catalyst composition for preparing acrylic acid from acrolein, comprising a catalytic oxide on an inert porous carrier, said catalytic oxide having the composition of the formula $$Mo_a V_b Z_c W_d Cu_e$$

wherein Z is at least one alkaline earth metal atom selected from the group consisting of beryllium, magnesium, calcium, barium and strontium; $a$, $b$, $c$, $d$, and $e$ are the numbers of the respective metal atoms; when $a$ is 12, $b$ is 2 to 14, $c$ is 0.1 to 6, $d$ is 0 to 12, and $e$ is 0 to 6, with the proviso that $d$ plus $e$ is not 0, and a process for preparing acrylic acid by the catalytic vapor-phase oxidation of acrolein with a gas containing molecular oxygen in the presence of such catalyst.

10 Claims, No Drawings

PROCESS FOR PREPARING ACRYLIC ACID

This invention relates to a process for preparing acrylic acid, and a catalyst composition for use in this process. More specifically, the invention relates to a process for preparing acrylic acid by the catalytic vapor-phase oxidation of acrolein over a catalyst using a gas containing molecular oxygen, and to a catalyst composition capable of yielding acrylic acid which has high quality and can be easily purified.

The commercial production of acrylic acid by the catalytic vapor-phase oxidation of acrolein generally requires that the catalyst composition used should bring about a high conversion of acrolein and a high selectivity to acrylic acid, and that it can be prepared with relative ease and can retain its catalytic activity stably over prolonged periods of time. However, a stronger requirement of the catalyst composition would be that it should permit the formation of high quality acrylic acid capable of being easily purified.

Conventional acrylic acid produced by the catalytic vapor-phase oxidation of propylene or acrolein contains traces of impurities which cannot be separated by a mere rectifying procedure, and the presence of such impurities often causes unexpected troubles. In particular, when such acrylic acid is used for a polymerization reaction, various troubles occur. For example, a long period of time is required until the completion of the polymerization reaction, or the reaction time required varies over a considerably wide range. It is difficult to add a polymerization initiator stably, and a high-molecular-weight polymer of good quality is difficult to prepare.

In order to remove these troubles, it has been necessary to work out a particular method for purifying acrylic acid obtained by a catalytic vapor-phase oxidation, according to an intended use of the acrylic acid.

A number of catalysts for preparing acrylic acid by the catalytic vapor-phase oxidation of acrolein have been known. For example, Japanese Patent Publication No. 1775/66 discloses a catalyst composition comprising molybdenum and vanadium, and Japanese Patent Publication No. 12129/69 discloses a catalyst composition comprising molybdenum, vanadium, tungsten and silica sol. These catalyst compositions, however, give only insufficient yields. The latter only gives a maximum one-pass yield of 87%. On the other hand, Japanese Patent Publication No. 26287/69 discloses a catalyst composition comprising molybdenum, vanadium, silver and copper; Japanese Patent Publication No. 24355/72 discloses a catalyst composition comprising molybdenum, vanadium, tungsten and manganese; and Japanese Patent Publication No. 6604/72 discloses a catalyst composition comprising molybdenum, vanadium and antimony. These catalyst compositions give improved one-pass yields of acrylic acid, but have not yet gained commercial acceptance because of the complexity in the catalyst preparation step (e.g., the catalyst should be pre-treated) or the economic disadvantage in the oxidation reaction step (e.g., the space velocity is at a low level).

It is an object of this invention therefore to provide a novel catalyst composition capable of being used for reaction at a high space velocity and giving acrylic acid of high quality in a high yield. Another object of this invention is to provide a process for preparing acrylic acid with commercial advantage using such a catalyst composition.

Other objects of this invention will become apparent from the following description.

We have found that a catalyst composition prepared by supporting on an inert porous carrier a catalytic oxide of the following composition:

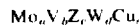

$Mo_a V_b Z_c W_d Cu_e$ wherein Z is at least one alkaline earth metal atom selected from the group consisting of beryllium, magnesium, calcium, barium and strontium; $a$, $b$, $c$, $d$ and $e$ represent the numbers of the respective metal atoms, and when a is 12, b is 2 to 14, preferably 4 to 12, c is 0.1 to 6, preferably 0.2 to 5, d is 0 to 12, preferably 0 to 10, and e is 0 to 6, preferably 0 to 4, with the proviso that $d$ plus $e$ is not 0, can achieve the objects of this invention. Thus, according to this invention, there are provided such a catalyst composition and a process for preparing acrylic acid by the catalytic vapor-phase oxidation of acrolein using this catalyst composition.

The oxygen is thought to be present in the catalytic oxide in the form of a complex metal oxide or a metallic acid salt and the oxygen content of the catalytic oxide accordingly varies depending upon the atomic ratio of the various metallic elements in the catalytic oxide.

The useful inert porous carrier to support the catalytic oxide in this invention is, for example, a pulverized product or granulated pellets of α-alumina, silicon carbide, pumice, silica, zirconia, or titanium oxide. A material which is not porous by itself but can be formed into porous pellets by granulation can also be used as a material for the carrier used in this invention. An example of such a material is glass. Preferably, the carrier has a surface area of not more than 2 m²/g, a porosity of 10 to 65%, and a pore distribution such that at least 80% of all the pores have a particle diameter of 1 to 1500 microns. Especially preferred carriers are those having a surface area of not more than 1 m²/g, a porosity of 30 to 65%, and a pore distribution such that at least 90% of all the pores have a particle diameter of 1 to 1500 microns.

The catalyst composition of this invention is prepared, for example, by adding a carrier to an aqueous solution having dissolved therein a molybdenum compound such as ammonium molybdate, a vanadium compound such as ammonium metavanadate, an alkaline earth metal compound such as strontium nitrate, a tungsten compound such as ammonium para-tungstate, and a copper compound such as copper nitrate, evaporating the aqueous solution to dryness, and calcining the dried product at 300° to 800°C., preferably 350° to 600°C. Of course, the starting metal compounds are not limited to the ammonium salts or nitrates as illustrated above, but all of the metal oxides, organic acid-metal salts, inorganic acid-metal salts, metal complex compounds, and organic metal compounds, etc. can be utilized if they can be calcined to form a catalytic oxide.

The process for preparing acrylic acid from acrolein in accordance with this invention is carried out by passing a gaseous mixture consisting of 1 to 10% by volume of acrolein, 1 to 15% by volume of oxygen, 5 to 60% by volume of steam and 20 to 80% by volume of an inert gas over the catalyst composition described above at a temperature of 200° to 350°C. and a pressure of atmospheric pressure to 10 atmospheres at a space velocity of 500 to 8,000 hr$^{-1}$(NTP). The starting gas may also be an acrolein-containing gas resulting from the direct oxidation of propylene, or a mixture of it with air or oxygen. It has been confirmed that by-products contained in such an acrolein-containing gas, for example, acrylic acid, acetaldehyde acetic acid, carbon dioxide or carbon monooxide, or unreacted substances such as propylene or propane do not adversely affect the process of this invention.

The catalyst composition of this invention can be used effectively not only in a fixed bed reaction, but also in a fluidized bed reaction.

Acrylic acid prepared by the process of this invention is of very good quality, and can be simply purified by customary purification procedures to form acrylic acid of stable quality free from impurities.

The following Examples and Comparative Examples illustrate the present invention in greater detail, but it should be noted that these examples do not limit the present invention.

The conversion, selectivity and one-pass yield in the following examples are defined as follows:

$$\text{Conversion (mol\%)} = \frac{\text{Moles of acrolein reacted}}{\text{Moles of acrolein fed}} \times 100$$

$$\text{Selectivity (mol\%)} = \frac{\text{Moles of acrylic acid formed}}{\text{Moles of acrolein reacted}} \times 100$$

$$\text{One-pass yield (mol\%)} = \frac{\text{Moles of acrylic acid formed}}{\text{Moles of acrolein fed}} \times 100$$

EXAMPLE 1

Preparation of Catalyst

To 2,500 ml. of water being heated and stirred, were added 52 g of ammonium para-tungstate, 43g of ammonium metavanadate, 169 g of ammonium molybdate and 8.6 g of strontium nitrate. The resulting aqueous solution was mixed with an aqueous solution of 43 g of copper nitrate in 500 ml. of water. The resulting mixed solution was placed in a porcelain evaporator on a water bath, and 500 ml. of a carrier consisting of granular α-alumina particles having a particle diameter of 3 to 5 mm was added, followed by mixing with stirring. The mixture was evaporated to dryness therein to deposit each of the above compounds on the carrier, and then calcined at 400°C. for 5 hours. The metal composition of the resulting catalytic oxide was as follows:

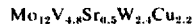

$Mo_{12}V_{4.8}Sr_{0.5}W_{2.4}Cu_{2.2}$

The carrier used above had a surface area of not more than 1 m$^2$/g, a porosity of 42%, and a pore distribution such that 92% of all the pores have a particle diameter of 30 to 250 microns.

Reaction

A stainless steel U-shaped tube having a diameter of 25 mm was charged with 400 ml. of the catalyst composition prepared above, and immersed in a nitre bath (molten nitric acid salt) heated at 255°C. A gaseous mixture consisting of 4% by volume of acrolein, 51% by volume of air and 45% by volume of steam was passed through the tube and was reacted at a space velocity of 3,000 hr$^{-1}$ (NTP). The results obtained are shown in Table 1.

Purification

The gas formed as a result of the reaction was passed through a condenser-collector to obtain an aqueous solution of about 20% crude acrylic acid. The condensed liquid was then extracted with ethyl acetate with the liquid-to-solvent ratio of 1:1 by volume. The organic liquid phase obtained was fed to a distillation tower, and the solvent and light-boiling substances were stripped. Crude acrylic acid obtained from the bottom of the tower was fed into an oldershaw distillation tower having 10 trays, and rectified while maintaining the pressure at the top of the tower at 70 mmHg, the temperature at the top of the tower at 77.5°C., and the reflux ratio at 1.0.

Polymerization test

The resulting purified acrylic acid (containing 100 ppm of hydroquinone monomethyl ether as a stabilizer) was diluted to 50% by volume with deionized water, and placed in a test tube 16 mm in diameter and 180 mm in length together with 0.04% by weight, based on the acrylic acid, of ammonium persulfate as a polymerization initiator. The polymerization was carried out in an oil bath maintained at 70°C. The time required from the immersion of the test tube in the oil bath to the reaching of the maximum heat-generating temperature was found to be 15 minutes.

In this polymerization test, the time required to attain the maximum heat-generating temperature is shorter for such an acrylic acid that is more stable in storage and contains lesser amounts of impurities. When high quality acrylic acid permitting a shorter time required to attain the maximum heat-generating temperature is used in a polymerization reaction, the conversion is high, and a high molecular weight polymer can be obtained at low catalyst concentrations.

Stability test

To the purified acrylic acid obtained above was added 0.02% by weight of hydroquinone monomethyl ether, and the mixture was placed in a sealed tube having a diameter of 16 mm and a length of 120 mm. The tube was then placed in an oil bath keeping the temperature at 80°C. After a lapse of 9 hours, no polymer was observed.

Comparative Example 1

The procedure of Example 1 was repeated except that ammonium para-tungstate, strontium nitrate and copper nitrate were not used. A catalyst composition containing a catalytic oxide of the following metal composition $Mo_{12} V_{4.8}$ was obtained. Using this catalyst composition, the same reaction as in Example 1 was performed. The results obtained are shown in Table 1.

Comparative Example 2

The procedure of Example 1 was repeated except that ammonium para-tungstate and copper nitrate were not used. A catalyst composition containing a catalytic oxide having the following metal composition

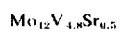

$Mo_{12}V_{4.8}Sr_{0.5}$ was obtained. The same reaction as in Example 1 was performed using the resulting catalyst composition. The results are shown in Table 1.

Comparative Example 3

The same procedure as in Example 1 was performed except that strontium nitrate was not used. A catalyst composition containing a catalytic oxide of the following metal composition $$Mo_{12}V_{4.8}W_{2.4}Cu_{2.2}$$

was obtained.

Using this catalyst composition, the same reaction as in Example 1 was carried out. The results obtained are shown in Table 1. The crude acrylic acid was purified in the same way as in Example 1 to form purified acrylic acid. The purified acrylic acid was subjected to the same polymerization test and stability test as in Example 1, and it was found that the time required for attaining the maximum heat-generating temperature was 45 minutes, and the formation of polymer was not observed even after a lapse of 9 hours.

The condensed liquid obtained from the reaction gas was purified in the same way as in Example 1, and the purified acrylic acid was subjected to the same polymerization test and stability test as in Example 1. It was found that the time required to attain the maximum heat-generating temperature was 20 minutes, and the formation of polymer was not observed even after a lapse of 9 hours.

EXAMPLE 4

The same reaction as in Example 1 was performed using a gaseous mixture consisting of 5% by volume of acrolein, 50% by volume of air and 45% by volume of steam at a space velocity of 3,500 $hr^{-1}$. The conversion of acrolein was 100%, the selectivity to acrylic acid was 97.3%, and the one-pass yield of acrylic acid was 97.3%.

The condensed liquid obtained from the reaction gas was purified in the same way as in Example 1, and the purified acrylic acid was subjected to the same polymerization test and stability test as in Example 1. It was found that the time required to attain the maximum heat-generating temperature was 15 minutes, and the formation of polymer was not observed even after a Table 1

| Example and Comparative Examples | Composition of catalyst (atomic ratio) | | | | | Nitre bath temperature (°C.) | Space velocity ($hr^{-1}$) | Conversion of acrolein (mole%) | Acrylic acid | |
|---|---|---|---|---|---|---|---|---|---|---|
| | Mo | V | Sr | W | Cu | | | | Selectivity (mol%) | One-pass yield (mol%) |
| Example 1 | 12 | 4.8 | 0.5 | 2.4 | 2.2 | 255 | 3,000 | 100 | 97.5 | 97.5 |
| Comparative Example 1 | 12 | 4.8 | 0 | 0 | 0 | 255 | 3,000 | 36.0 | 52.0 | 18.7 |
| Comparative Example 2 | 12 | 4.8 | 0.5 | 0 | 0 | 255 | 3,000 | 38.0 | 92.0 | 35.0 |
| Comparative Example 3 | 12 | 4.8 | 0 | 2.4 | 2.2 | 255 | 3,000 | 98.5 | 97.0 | 95.5 |

EXAMPLE 2

The same reaction as in Example 1 was performed except that the nitre bath temperature was maintained at 260°C., and the space velocity was changed to 4,000 $hr^{-1}$. The conversion of acrolein was 98.5%, the selectivity to acrylic acid was 97.8%, and the one-pass yield of acrylic acid was 96.3%.

The condensed liquid obtained from the reaction gas was purified in the same way as in Example 1, and the purified acrylic acid was subjected to the same polymerization test and stability test as in Example 1. It was found that the time required to attain the maximum heat-generating temperature was 15 minutes and the formation of polymer was not observed even after a lapse of 9 hours.

EXAMPLE 3

The same reaction was carried out as in Example 1 except that the nitre bath temperature was maintained at 265°C., and the space velocity was changed to 5,000 $hr^{-1}$. The conversion of acrolein was 97.5%, the selectivity to acrylic acid was 98.5%, and the one-pass yield of acrylic acid was 96.0%.

lapse of 9 hours.

EXAMPLE 5

The same reaction as in Example 4 was performed using a gaseous mixture consisting of 7% by volume of acrolein, 48% by volume of air and 45% by volume of steam. The conversion of acrolein was 99.1 %, the selectivity to acrylic acid was 97.0%, and the one-pass yield of acrylic acid was 96.1%.

The condensed liquid obtained from the reaction gas was purified in the same way as in Example 1, and purified acrylic acid was subjected to the same polymerization test and stability test as in Example 1. It was found that the time required to attain the maximum heat-generating temperature was 20 minutes, and the formation of polymer was not observed even after a lapse of 9 hours.

EXAMPLES 6 TO 12

Catalyst compositions were prepared in the same way as in Example 1 using various alkaline earth metals, and the reaction was performed under various reaction conditions. The results obtained are shown in Table 2.

As for the Z component in Table 2, a fine powder of oxide was used as an Mg component, and Be, Ca, Ba and Sr components were used as nitrates.

mercial grade propylene (purity more than 94%) in the presence of a molybdenum-bismuth catalyst.

Composition of the gaseous mixture

Table 2

| Examples | Composition of catalyst (atomic ratio) | | | | | Nitre bath tempe- rature (°C) | Space velocity (hr⁻¹) | Con- version of acrolein (mole%) | Acrylic acid | |
|---|---|---|---|---|---|---|---|---|---|---|
| | Mo | V | Z | W | Cu | | | | Selectivi- ty (mole%) | One-pass yield (mole%) |
| 6 | 12 | 4.8 | Be 0.5 | 2.4 | 2.2 | 245 | 2,000 | 98.1 | 98.0 | 96.1 |
| 7 | 12 | 4.8 | Mg 1.0 | 1.2 | 2.2 | 241 | 2,000 | 100 | 97.0 | 97.0 |
| 8 | 12 | 7 | Ca 2.2 | 4.8 | 3.0 | 238 | 2,000 | 99.3 | 97.2 | 96.5 |
| 9 | 12 | 10 | Ba 2.2 | 9 | 2.2 | 243 | 2,000 | 99.5 | 98.2 | 97.7 |
| 10 | 12 | 4.8 | Sr 0.5 Ba 0.5 | 2.0 | 2.2 | 244 | 2,000 | 100 | 97.5 | 97.5 |
| 11 | 12 | 6 | Sr 3.5 | 3.0 | 0 | 243 | 2,000 | 94.5 | 97.0 | 91.7 |
| 12 | 12 | 8 | Sr 4.0 | 0 | 3.0 | 240 | 2,000 | 93.6 | 98.3 | 92.0 |

The condensed liquid obtained from the reaction gas in each of Examples 6 to 12 was purified in the same way as in Example 1, and the purified acrylic acid was subjected to the polymerization test and stability test in the same way as in Example 1. It was found that the time required to attain the maximum heat-generating temperature was 16 minutes, 18 minutes, 20 minutes, 18 minutes, 17 minutes, 18 minutes and 16 minutes, respectively, and in each Example, the formation of polymer was not observed after a lapse of 9 hours.

EXAMPLE 13

The same procedure as in Example 1 was repeated except using a carrier composed of silicon carbide granules having a diameter of 3 to 5 mm, a specific surface area of not more than 1 m²/g, a porosity of 41%, and a pore distribution such that 90% of all the pores have a particle diameter of 5 to 80 microns.

The conversion of acrolein was 99.5%, the selectivity to acrylic acid was 97.4%, and the one-pass yield of acrylic acid was 96.9%.

The condensed liquid obtained from the reaction gas was purified in the same way as in Example 1, and the purified acrylic acid was subjected to the same poly- merization test and stability test as in Example 1. It was found that the time required to attain the maximum heat-generating temperature was 15 minutes, and the formation of polymer was not observed even after a lapse of 9 hours.

EXAMPLE 14

A gaseous mixture of the following composition was obtained by catalytic vapor-phase oxidation of com-

| | |
|---|---|
| Acrolein | 5.01 % by volume |
| Propylene + propane | 0.58% by volume |
| Acrylic acid + acetic acid | 0.60% by volume |
| Nitrogen | 51% by volume |
| Oxygen | 6.50% by volume |
| Steam | 34.0% by volume |
| Others | 2.31% by volume |

The gaseous mixture was introduced into a reaction tube packed with the same catalyst composition as used in Example 1, and reacted at a space velocity of 3,000 hr⁻¹ while maintaining the temperature of the nitre bath at 225°C.

The conversion of acrolein was 99.7%, the selectivity to acrylic acid was 97.5%, and the one-pass yield of acrylic acid was 97.2%. In calculating these values, it was assumed that propylene, propane and acrylic acid did not react.

The condensed liquid obtained from the reaction gas was purified in the same way as in Example 1, and the purified acrylic acid was subjected to the same poly- merization test and stability test as in Example 1. It was found that the time required to attain the maximum heat-generating temperature was 21 minutes, and the formation of polymer was not observed after a lapse of 9 hours.

EXAMPLES 15 TO 18

Catalyst compositions were prepared in the same way as in Example 1 except that the carrier shown in Table 3 were used.

Using these catalyst compositions, the reaction was carried out in the same way as in Example 1. The purifi- cation, the polymerization test, and the stability test were performed in the same way as in Example 1. The results obtained are shown in Table 4.

Table 3

| Examples | Carrier | | | | |
|---|---|---|---|---|---|
| | Material | Surface area | Pore volume | Pore distribution | Particle diameter |
| Example 15 | α-alumina(50%) SiC | < 1 m²/g | 47% | (75–1000μ) 95% | 3 – 5 mm |
| Example 16 | α-alumina(75%) Silica | < 1 m²/g | 40% | (50–1200μ) 95% | 3 – 5 mm |
| Example 17 | SiC | < 1 m²/g | 55% | (75–500μ) 93% | 3 – 5 mm |
| Example 18 | α-alumina(85%) Silica | < 1 m²/g | 35% | (20–180 μ) 100% | 3 – 5 mm |

Table 4

| Examples | Composition of catalyst (atomic ratio) | | | | | Nitre bath temperature (°C) | Space velocity (hr$^{-1}$) | Conversion of acrolein (mole%) | Acrylic acid | | Polymerization test* (minutes) | Stability test |
|---|---|---|---|---|---|---|---|---|---|---|---|---|
| | Mo | V | Sr | W | Cu | | | | Selectivity (mole%) | One-pass yield (mole%) | | |
| Example 15 | 12 | 4.8 | 0.5 | 2.4 | 2.2 | 255 | 3,000 | 99.6 | 97.4 | 97.0 | 16 | The formation of polymer was not observed after a lapse of 9 hours |
| Example 16 | 12 | 4.8 | 0.5 | 2.4 | 2.2 | 255 | 3,000 | 98.8 | 97.6 | 96.4 | 18 | do. |
| Example 17 | 12 | 4.8 | 0.5 | 2.4 | 2.2 | 255 | 3,000 | 99.4 | 97.3 | 96.7 | 16 | do. |
| Example 18 | 12 | 4.8 | 0.5 | 2.4 | 2.2 | 255 | 3,000 | 99.0 | 97.5 | 96.5 | 17 | do. |

*Time required to attain the maximum heat-generating temperature.

What we claim is:

1. A process for preparing acrylic acid which comprises catalytically oxidizing acrolein with a gas containing molecular oxygen in the vapor phase in the presence of a catalyst composition consisting essentially of a catalytic oxide supported on an inert porous carrier, prepared by depositing compounds of each of the metallic elements of said catalytic oxide on the carrier and calcining the compounds and carrier at a temperature of 300° to 800°C, said catalytic oxide having the composition of the formula

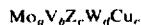

$$Mo_a V_b Z_c W_d Cu_e$$

wherein Z is at least one alkaline earth metal atom selected from the group consisting of beryllium, magnesium, calcium, barium and strontium; $a$, $b$, $c$, $d$ and $e$ represent the numbers of the respective metal atoms; and when $a$ is 12, $b$ is 2 to 14, $c$ is 0.1 to 6, $d$ is 0 to 12, and $e$ is 0 to 6, with the proviso that $d$ plus $e$ is not 0 and an oxygen content dependent on the atomic ratios of the metallic elements of the catalytic oxide.

2. The process of claim 1 wherein said inert porous carrier has a surface area of not more than 2 m²/g, a porosity of 10 to 65%, and a pore distribution such that at least 80% of the entire pores have a particle diameter of 1 to 1500 microns.

3. The process of claim 1 wherein whan $a$ is 12, $b$ is 4 to 12, $c$ is 0.2 to 5, $d$ is 0 to 12 and $e$ is 0 to 4, with the proviso that $d + e$ is not 0.

4. The process of claim 1 wherein said catalyst composition is prepared by adding the carrier to an aqueous solution having dissolved therein compounds of each of the metallic elements of said catalytic oxide, evaporating the aqueous solution to dryness and calcining the dried product at a temperature of 300° to 800°C.

5. The process of claim 1 wherein said inert porous carrier is selected from the group consisting of alpha-alumina, silicon carbide, pumice, silica, zirconia and titanium oxide.

6. The process of claim 8 wherein said inert porous carrier has a surface area of not more than 1 m²/g, a porosity of 30 to 65%, and a pore distribution such that at least 90% of all the pores have a particle diameter of 1 to 1500 microns.

7. The process of claim 2 wherein said vapor phase oxidation reaction is carried out at a temperature of 200° to 350°C at a pressure of 1 atmosphere to 10 atmospheres and at a space velocity of 500 to 8,000 hr$^{-1}$.

8. The process of claim 1 wherein the catalytic oxide contains tungsten.

9. The process of claim 1 wherein the catalytic oxide contains copper.

10. The process of claim 1 wherein the catalytic oxide contains tungsten and copper.

* * * * *